(12) United States Patent
Guthrie et al.

(10) Patent No.: US 6,866,869 B2
(45) Date of Patent: Mar. 15, 2005

(54) LIQUID ANTIMICROBIAL COMPOSITIONS

(75) Inventors: Walter Graham Guthrie, Loughborough (GB); Mohammed Shoaib Qureshi, Bingham (GB); Lawrence Alan Staniforth, Sneinton (GB); Darren Michael Hodgkinson, Hucknall (GB); David Wilson Ashworth, Lowdham (GB)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/250,566

(22) PCT Filed: Jan. 4, 2002

(86) PCT No.: PCT/GB02/00025

§ 371 (c)(1),
(2), (4) Date: Oct. 10, 2003

(87) PCT Pub. No.: WO02/054872

PCT Pub. Date: Jul. 18, 2002

(65) Prior Publication Data

US 2004/0052778 A1 Mar. 18, 2004

(30) Foreign Application Priority Data

Jan. 10, 2001 (GB) .............................................. 0100643

(51) Int. Cl.$^7$ ........................ A61K 33/18; A61K 33/00; A61K 38/44; A01N 59/12; A01N 59/24

(52) U.S. Cl. .................... 424/609; 424/94.1; 424/94.4; 424/607; 424/608; 424/667; 424/669; 424/670; 424/671; 514/514; 514/515; 422/29

(58) Field of Search ................................ 424/94.1, 94.4, 424/607–609, 667, 669–671; 514/514, 515; 422/29

(56) References Cited

U.S. PATENT DOCUMENTS 5,972,355 A  * 10/1999  Knight et al. ................ 424/401
6,576,227 B1 *  6/2003  Montgomery ................. 424/50

FOREIGN PATENT DOCUMENTS

| DE | 43 01 277 | 7/1994 |
| WO | 91/11105 | 8/1991 |
| WO | 95/26137 | 10/1995 |

* cited by examiner

Primary Examiner—John Pak
(74) Attorney, Agent, or Firm—Keil & Weinkauf

(57) ABSTRACT

A liquid antimicrobial composition comprises:
 (1) a mixture of iodide anions and thiocyanate anions;
 (2) periodic acid or an alkali metal salt thereof; and
 (3) optionally, a peroxidase.

The composition may be used as a microbicide, disinfectant or for suppressing or killing viruses or spores.

17 Claims, No Drawings

LIQUID ANTIMICROBIAL COMPOSITIONS

This application is a 371 of PCT/GB02/00025, filed on Jan. 4, 2000.

This invention relates to an antimicrobial composition comprising iodide and thiocyanate anions.

Particular compositions of this type are disclosed in WO-A-91/11105. These compositions comprise
(1) iodide and thiocyanate anions in a weight:weight ($I^-$:$SCN^-$) ratio of 0.1:1 to 50:1 and in a combined anion weight concentration of at least 5 mg/kg;
(2) D-glucose in a weight concentration of at least 0.2 g/kg;
(3) glucose oxidase as an oxidoreductase enzyme; and
(4) optionally, a peroxidase, especially lactoperoxidase.

Preferred such compositions of WO-A-91/11105 are preservative compositions in a solid (dry powder), or liquid two-pack form in which one pack contains the D-glucose and the other the glucose oxidase. The contents of the two packs are mixed and immediately used.

On the other hand WO-A-95/26137 describes antimicrobial compositions containing the same components as those of WO-A-91/11105 and preferably in the same proportions. However, WO-A-95/26137 does not recommend the immediate use of components mixed together; rather, it teaches the provision of an incubation period of from 12–48 hours before use. From this, it is clear that in order to achieve an antimicrobial effect using such compositions, it is necessary to allow the components to react with one another to form a reaction product which then has the desired rapid antimicrobial activity.

As an alternative to compositions containing iodide and thiocyanate anions, antimicrobial compositions are known which are based on periodic acid, which is a known oxidising agent and electron acceptor. For example, DE-A-4301277 describes the use of periodic and/or orthoperiodic acid for the sterilisation of containers for storage and transportation of milk by treating the internal surfaces of the container at room temperature for 2–20 seconds with an aqueous solution of 0.1 to 5 wt % of periodic or orthoperiodic acid.

EP-A-0726357 describes a process for inhibiting the production and accumulation of volatile fatty acids by hydrolytic fermentative bacteria in an anionic pulp and paper processing stream in which the presence of hydrogen is monitored and at least one of a biocide and an electron acceptor is added. The use of sodium (para) periodate is recommended for the case where the presence of an electron acceptor and some inhibition of the microorganisms is required.

We have now found surprisingly that if, in an antimicrobial composition containing iodide and thiocyanate ions, D-glucose and glucose oxidase (such as a composition described in WO-A-91/11105 or WO-A-95/26137), the D-glucose and glucose oxidase in combination are replaced solely by periodic acid or an alkali metal salt thereof, an efficient liquid antimicrobial composition is obtained, which is capable of having a rapid killing effect upon the microorganisms which it is used to treat.

Thus, according to one aspect, the invention provides a liquid antimicrobial composition comprising
(1) a mixture of iodide anions and thiocyanate anions;
(2) periodic acid or an alkali metal salt thereof; and
(3) optionally, a peroxidase.

Periodic acid [CAS RN 10450-60-9], sometimes referred to an orthoperiodic acid, has the formula

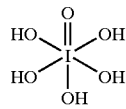

Preferably, the periodic acid or salt thereof is present in the composition in an amount of from 25 to 500 ppm, more preferably from 200 to 500 ppm, by weight of the total weight of the composition.

Thus, even a composition containing as low an amount of periodic acid as 25–50 ppm can kill bacteria such as *E. coli* but for a broad spectrum of activity, the minimum amount should be about 100 ppm. Moreover, for a stable shelf life, at least 200 ppm is preferred. The preferred maximum amount is about 500 ppm.

Such compositions react considerable faster than the composition disclosed in WO-A-91/11105 and WO-A-95/26137 so that, instead of the 4–48 hours recommended for optimum potency, compositions embodying the invention may achieve a rapid kill of microorganisms immediately after mixing.

In contrast to the two-pack forms disclosed in WO-A-91/11105 and WO-A-95/26137 for use as a preservative, a liquid composition embodying the invention can be used as a disinfectant, in the form of a single, ready to use, product.

The spectrum of antimicrobial activity is also somewhat different from that of the abovementioned known compositions. In particular, compositions embodying the invention are particularly effective in combatting viruses and spores, e.g. *bacillus* spores.

The precise role played by the periodic acid in improving the antimicrobial efficiency of the iodide/thiocyanate anion system is not fully understood, although the mechanism seems to involve oxidation.

The pH of the composition may be from, say, 1 to 8 but is preferably less than 4.5 and, especially at low pH, the composition may contain free periodic acid. However, the composition may alternatively or additionally contain an alkali metal, especially the sodium, salt thereof.

As indicated above, the composition may additionally contain a peroxidase, especially lactoperoxidase; the presence of a peroxidase is surprisingly found to improve the shelf life of the composition. Thus, although this might have been expected for an organic oxidation/reduction system as in WO-A-91/11105, it is surprising that such an effect is achievable with an inorganic system utilizing periodic acid.

Preferably the peroxidase is present in the composition in an amount of at least 10 U/kg.

In a composition embodying the invention, the weight:weight ratio of iodide:thiocyanate anions is preferably from 0.1:1 to 50:1, more preferably from 0.2:1 to 20:1 inclusive.

The iodide and thiocyanate anions are preferably present in the composition in a total amount of at least 5 mg/kg, based on the total weight of the composition. The iodide anions are preferably present in the composition at a weight concentration of at least 5 mg/kg, while the thiocyanate ions are preferably present at a weight concentration of at least 2 mg/kg, based on the total weight of the composition.

A composition embodying the invention may contain additionally a suitable carrier. Preferably, the carrier is water and the composition is an aqueous solution. However, the carrier may comprise water and, additionally, a surfactant or emulsifier, whereby the composition is an oil in water emulsifier or a surfactant based solution.

According to other aspects, the invention provides the use of a composition as defined above as a microbicide or as a disinfectant respectively and especially the use of such a composition for suppressing or killing viruses or spores, e.g. *bacillus* spores.

In addition to the use of the composition as a microbicide or disinfectant, an anti-microbial composition embodying the invention may provide the active component in a wide variety of products which require potent antibacterial, anti-mould and/or anti-yeast activities. Examples of such products include:
a) deodorants e.g. for topical administration in the form of lotions;
b) antibacterial skin washes e.g. in the forms of lotions;
c) anti-acne preparations e.g. in the form of lotions or creams;
d) anti-athletes foot preparations e.g. in the form of lotions;
e) anti-dandruff preparations e.g. in the form of shampoos or lotions;
f) dental preparations, e.g. mouth washes suitable for general oral hygiene and, in particular, having anti-plaque properties, and dentrifices such as toothpastes, chewing gums and lozenges;
g) impregnated materials e.g. wound dressings, sutures and dental floss;
h) pharmaceuticals e g. wound irrigants and burn treatments, anti-diarrhoeal agents and medicaments suitable for the treatment of infections such as *Candida* and *Tinea* infections;
i) opthalmic preparations e.g. eye washes and/or sterilising contact lenses; and
j) sterilants e.g. for baby bottles and surgical or dental instruments.

According to yet another aspect, the invention provides a method of killing or suppressing viruses or spores comprising contacting them within a composition as defined above.

Embodiments of the invention will now be described in more detail with reference to the following Examples.

EXAMPLE

A composition contains
1. NaSCN 4.2 mg
2. KI 7.3 mg
3. Lactoperoxidase 70 international units
4. Periodic acid 200 mg
5. Water up to 100 ml.

Components 1–4 were added to 75 mls of distilled water and stirred until dissolved. The solution was then made up to 100 mls with distilled water.

The above solution was then immediately challenged with a $1 \times 10^6$ cfu/ml inoculum of the following organisms.
*Ps. aeruginosa* NCIB 8626
*S. aureus* NCIB 9518
*E. coli* NCIB 8545
*C. albicans* ATCC 1023
*A. niger* ATCC 16404

Total kill of each of the above organisms was achieved in less than 5 mins.

Excellent anti-viral activity was also demonstrated against Echovirus 11 and Herpes simplex virus type 1 (HSV-1).

Excellent sporicidal activity was also demonstrated against *B. cereus* NCTC 2599 and *B. subtilis* NCTC 10073.

The solution was still demonstrating the above activity after six months storage at room temperature.

What is claimed is:

1. A liquid antimicrobial composition comprising:
   (1) a mixture of iodide anions and thiocyanate anions;
   (2) periodic acid or an alkali metal salt thereof; and
   (3) optionally, a peroxidase.

2. A composition according to claim 1, containing a salt of periodic acid, which salt is an alkali metal salt.

3. A composition according to claim 2, wherein the periodic acid or salt thereof is present in an amount of from 200 to 500 ppm by weight of the total weight of the composition.

4. A composition according to any preceding claim, wherein the weight:weight ratio of iodide:thiocyanate anions is from 0.1:1 to 50:1 inclusive.

5. A composition according to claim 4, wherein the weight:weight ratio of iodide:thiocyanate anions is from 0.2:1 to 20:1 inclusive.

6. A composition according to claim 5, wherein the weight:weight ratio of iodide:thiocyanate anions is from 0.2:1 to 20:1 inclusive.

7. A composition according to claim 1, wherein the iodide and thiocyanate anions are present in the composition in a total weight of at least 5 mg/kg, based on the total weight of the composition.

8. A composition according to any preceding claim, which contains a peroxidase.

9. A composition according to claim 8, wherein the peroxidase is lactoperoxidase.

10. A composition according to claim 8 or claim 9, wherein the peroxidase is present in the composition in an amount of at least 10 U/kg.

11. A composition according to claim 9, wherein the peroxidase is present in the composition in an amount of at least 10 IU/kg.

12. A composition according to claim 11, wherein the carrier is water and the composition is an aqueous solution.

13. A composition according to claim 12, wherein the carrier additionally comprises a surfactant or emulsifier and the composition is an oil in water emulsifier or a surfactant based solution.

14. A composition according to claim 13, wherein the carrier additionally comprises a surfactant or emulsifier and the composition is an oil in water emulsion or a surfactant based solution.

15. Use of a composition according to any one of claims 1 to 13 as a disinfectant.

16. Use of a composition according to any one of claims 1 to 14 for suppressing or killing viruses or spores.

17. A method of killing or suppressing viruses or spores comprising contacting them with an effective amount of a composition according to claim 1.

* * * * *

UNITED STATES PATENT AND TRADEMARK OFFICE
CERTIFICATE OF CORRECTION

PATENT NO. : 6,866,869 B2
APPLICATION NO. : 10/250566
DATED : March 15, 2005
INVENTOR(S) : Guthrie et al.

It is certified that error appears in the above-identified patent and that said Letters Patent is hereby corrected as shown below:

Column 1, line 4, "Jan. 4, 2000" should read --Jan. 4, 2002--.

Col. 4, line 5-10, cancel claim 1, and insert the following claim:

1. A liquid antimicrobial composition comprising:
(1) a mixture of Iodide anions and thiocyanate anions;
(2) periodic acid or a salt thereof; and
(3) optionally, a peroxidase.

Col. 4, lines 13-16, cancel claim 3, and insert the following claim:

3. A composition according to claim 1, wherein the periodic acid or salt thereof is present in the composition in an amount of from 25 to 500 ppm by weight of the total weight of the composition.

Col. 4, lines 17-20, cancel claim 4, and insert the following claim:

4. A composition according to claim 3, wherein the periodic acid or salt thereof is present in an amount of from 200 to 500 ppm by weight of the total weight of the composition.

Col. 4, lines 21-23, cancel claim 5, and insert the following claim:

5. A composition according to claim 1, wherein the weight:weight ratio of iodide:thiocyanate anions is from 0.1:1 to 50:1 inclusive.

Col. 4, lines 31-32, cancel claim 8, and insert the following claim:

8. A composition according to claim 1, wherein the iodide anions are present in the composition to a weight concentration of at least 5 mg/kg and the thiocyanate ions to a weight concentration of at least 2 mg/kg, based on the total weight of the composition.

Col. 4, lines 33-34, cancel claim 9, and insert the following claim:

9. A composition according to claim 1, which contains a peroxidase.

Col. 4, lines 35-37, cancel claim 10, and insert the following claim:

10. A composition according to claim 9, wherein the peroxidase is lactoperoxidase.

UNITED STATES PATENT AND TRADEMARK OFFICE
CERTIFICATE OF CORRECTION

PATENT NO. : 6,866,869 B2
APPLICATION NO. : 10/250566
DATED : March 15, 2005
INVENTOR(S) : Guthrie et al.

It is certified that error appears in the above-identified patent and that said Letters Patent is hereby corrected as shown below:

Col. 4, lines 41-42, cancel claim 12, and insert the following claim:

12. A composition according to claim 1 which additionally contains a suitable carrier.

Col. 4, lines 43-46, cancel claim 13, and insert the following claim:

13. A composition according to claim 12, wherein the carrier is water and the composition is an aqueous solution.

Col. 4, lines 51-52, cancel claim 15, and insert the following claim:

15. A microbicide comprising a composition according to claim 1.

Col. 4, lines 53-54, cancel claim, 16 and insert the following claim:

16. A disinfectant comprising of a composition according to claim 1.

Signed and Sealed this

Eleventh Day of September, 2007

JON W. DUDAS
*Director of the United States Patent and Trademark Office*